United States Patent [19]

Wehinger et al.

[11] Patent Number: 4,680,305
[45] Date of Patent: Jul. 14, 1987

[54] USE OF SULPHONYLDIHYDROPYRIDINES AS MEDICAMENTS FOR THE TREATMENT OF ASTHMA

[75] Inventors: Egbert Wehinger, Wuppertal, Fed. Rep. of Germany; Robertson Towart, Stoke Poges, United Kingdom

[73] Assignee: Bayer Aktiengesellschaft, Leverkusen, Fed. Rep. of Germany

[21] Appl. No.: 816,937

[22] Filed: Jan. 8, 1986

[30] Foreign Application Priority Data

Jan. 19, 1985 [DE] Fed. Rep. of Germany ....... 3501695

[51] Int. Cl.$^4$ ............................................. A61K 31/44
[52] U.S. Cl. .................................. 514/347; 514/334; 514/336; 514/338; 514/826
[58] Field of Search ................ 514/347, 334, 336, 338

[56] References Cited

U.S. PATENT DOCUMENTS 4,017,629 4/1977 Habicht et al. ................. 514/347 X

OTHER PUBLICATIONS

Chemical Abstracts, 88: 50661d, 1978, (Wehinger et al.).
Thorax, 38, 481–485, (1983), Barnes.

Primary Examiner—Leonard Schenkman
Attorney, Agent, or Firm—Sprung Horn Kramer & Woods

[57] ABSTRACT

A method of treating a patient suffering from asthma which comprises administering to such patient an asthma-relieving amount of a 5-sulphonyl-1,4-dihydropyridine of the formula

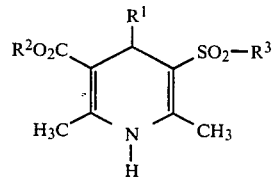

in which
$R^1$ is aryl having 6 or 10 C atoms, optionally substituted by 1 to 3 identical or different substituents from the group: halogen, cyano, nitro, trifluoromethyl, trifluoromethoxy, alkoxycarbonyl (up to 4 C atoms), carboxyl, alkoxy (up to 4 C atoms) or straight-chain or branched alkyl having up to 4 C atoms, or is heteroaryl, $R^2$ is straight-chain, branched or cyclic, saturated or unsaturated alkyl having up to 7 C atoms, which can be interrupted in the chain by 1 or 2 oxygen and/or sulphur atoms, and which is optionally substituted by halogen, nitro, cyano, carboxyl, alkoxycarbonyl (up to 4 C atoms), aryl (6 or 10 C atoms), or an amino group, it being possible for the amino group to carry 1 or 2 identical or different substituents from the group comprising alkyl (up to 4 C atoms), aryl (6 to 10 C atoms) or alkaryl (7 to 10 C atoms), $R^3$ is aryl (6 to 10 C atoms) which can optionally be substituted by 1 to 3 identical or different substituents from the group: halogen, cyano, nitro, trifluoromethyl, trifluoromethoxy, alkoxy (up to 4 C atoms), or dialkylamino, or is straight-chain, branched or cyclic alkyl having up to 8 C atoms, which can optionally be substituted by cyano, halogen or nitro. Some of the compounds are known.

6 Claims, No Drawings

USE OF SULPHONYLDIHYDROPYRIDINES AS MEDICAMENTS FOR THE TREATMENT OF ASTHMA

The present invention relates to the use of sulphonyl-1,4-dihydropyridines, some of which are known, for combating disorders of the respiratory tract, in particular to their use in medicaments having an anti-asthmatic effect.

It has already been disclosed that sulphonyl-1,4-dihydropyridines have a vasodilator effect and can be used as coronary therapeutic agents and agents having an antihypertensive effect (see German Offenlegungsschriften (German Published Specifications) Nos. 2,524,277, 2,616,995 and 2,639,498).

Furthermore, it has been disclosed that 1,4-dihydropyridine derivatives have protective effects for a variety of induced bronchial contractions (P. J. Barnes, Thorax 38, 481 (1983)).

However, the preferential effect of 5-sulphonyl-1,4-dihydropyridines on the bronchial musculature, which has now been found, is new and was unexpected from a knowledge of the state of the art.

It has been found that 5-sulphonyl-1,4-dihydropyridines of the general formula (I)

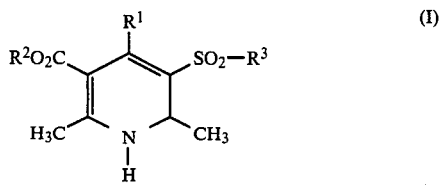

in which $R^1$ represents aryl having 6 or 10 C atoms, optionally substituted by 1 to 3 identical or different substituents from the group: halogen, cyano, nitro, trifluoromethyl, trifluoromethoxy, alkoxycarbonyl (up to 4 C atoms), carboxyl, alkoxy (up to 4 C atoms) or straight-chain or branched alkyl having up to 4 C atoms, or represents heteroaryl, $R^2$ represents straight-chain, branched or cyclic, saturated or unsaturated alkyl having up to 7 C atoms, which can be interrupted in the chain by 1 or 2 oxygen and/or sulphur atoms, and which is optionally substituted by halogen, nitro, cyano, carboxyl, alkoxycarbonyl (up to 4 C atoms), aryl (6 or 10 C atoms), or an amino group, it being possible for the amino group to carry 1 or 2 identical or different substituents from the group comprising alkyl (up to 4 C atoms), aryl (6 to 10 C atoms) or aralkyl (7 to 10 C atoms), $R^3$ represents aryl (6 to 10 C atoms) which can optionally be substituted by 1 to 3 identical or different substituents from the group: halogen, cyano, nitro, trifluoromethyl, trifluoromethoxy, alkoxy (up to 4 C atoms), or dialkylamino, or represents straight-chain, branched or cyclic alkyl having up to 8 C atoms, which can optionally be substituted by cyano, halogen or nitro, are particularly well suited for medicaments for asthma.

Preferred compounds are those of the general formula (I)
in which
$R^1$ represents phenyl which can optionally be substituted by 1 to 2 identical or different substituents from the group: fluorine, chlorine, bromine, nitro, cyano, trifluoromethyl, trifluoromethoxy, alkoxy (up to 2 C atoms) or alkyl (up to 2 C atoms), or represents pyridyl, thienyl, furyl or benzoxadiazolyl, $R^2$ represents straight-chain, branched or cyclic, saturated or unsaturated alkyl having up to 6 C atoms, which can optionally be interrupted in the chain by 1 to 2 oxygen and/or sulphur atoms, and which can optionally be substituted by 1 to 3 identical or different substituents from the group comprising fluorine, chlorine, bromine, cyano, nitro, alkoxycarbonyl (up to 2 C atoms), phenyl or an amino group, it being possible for the amino group to be substituted by one or two identical or different substituents from the group: alkyl (up to 2 C atoms) or benzyl, and $R^3$ represents phenyl which can optionally be substituted by 1 to 2 identical or different substituents from the group: fluorine, chlorine, bromine, nitro, trifluoromethyl, cyano, trifluoromethoxy or alkyl (up to 2 C atoms), or represents straight-chain, branched or cyclic alkyl (up to 7 C atoms) which can optionally be substituted by fluorine, chlorine, bromine, cyano or nitro.

Particularly preferred compounds are those of the general formula (I) in which
$R^1$ represents phenyl which is optionally substituted by 1 to 2 chlorine, cyano, nitro or trifluoromethyl, or represents pyridyl, $R^2$ represents straight-chain or branched alkyl having up to 5 C atoms, which can optionally be interrupted by an oxygen and/or sulphur atom, and which can optionally be substituted by one, two or three substituents from the group comprising fluorine, cyano or the benzylmethylamino group, and $R^3$ represents phenyl which is optionally substituted by 1 to 2 chlorine, nitro, cyano or trifluoromethyl, or represents methyl or ethyl, it being possible for ethyl optionally to be substituted by one to three fluorine, for use as medicaments for asthma.

Particularly suitable substances for use for asthma are ethyl 1,4-dihydro-2,6-dimethyl-5-phenylsulphonyl-4)-(2-trifluoromethylphenyl)pyridine-3-carboxylate, (2-ethylthio)ethyl 1,4-dihydro-2,6-dimethyl-5-methylsulphonyl-4-(3-nitrophenyl)pyridine-3-carboxylate and methyl 1,4-dihydro-2,6-dimethyl-5-methylsulphonyl-4-(2-nitrophenyl)pyridine-3-carboxylate.

Even after administration of low doses, the substances according to the invention act selectively on the bronchial musculature.

Because of their special properties, they are particularly suited for the treatment of asthma patients and thus represent an enrichment of pharmacy.

Some of the substances according to the invention and a few processes for the preparation of some of them are known (see German Offenlegungsschriften (German Published Specifications) 2,524,277, 2,616,995 and 2,639,498). They are preferably prepared by reaction of ylidene compounds of the formula (II)

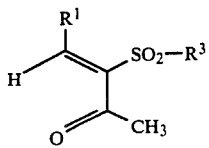

in which
R¹ and R³ have the abovementioned meanings, with aminocrotonic esters of the general formula (III)

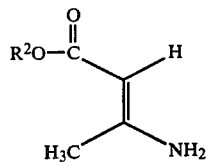

in which
R² has the abovementioned meaning, in the presence of inert solvents, in particular of lower aliphatic alcohols and of dimethylformamide, dimethyl sulphoxide, acetonitrile or hexamethylphosphoric triamide, at temperatures between 10° and 160° C., in particular between 20° and 120° C. The reaction is carried out, where appropriate, under an inert gas atmosphere, for example under nitrogen.

The compounds can be converted in a known manner into the customary formulations, such as tablets, capsules, coated tablets, granules, syrups, emulsions, suspensions, solutions and, in particular, inhalants, sprays or aerosols, using inert, non-toxic, pharmaceutically suitable vehicles, solvents or propellants. In each case, the therapeutically active compound should be present in these at a concentration of 0.5 to 90% by weight of the total mixture in order to reach the required dosage. Where appropriate, it is also possible to inhale the pure substance.

On parenteral administration, preferably amounts of from 0.001 to 1 mg/kg, in particular 0.001 to 0.1 mg/kg, of body weight are administered to achieve effective results. On oral administration, the dosage is preferably 0.01 to 10 mg/kg, in particular 0.1 to 5 mg/kg, of body weight per day. Where necessary it is possible to deviate from the amounts specified, and in fact to do so as a function of the body weight and of the specific mode of administration.

Moreover, the time of administration and the interval between individual administrations of specific formulations can determine a change in the dosage. Thus, it may suffice not only to make do with less than the minimum amount specified but also necessary in other cases to exceed the upper limit of the amounts specified.

The agents which can be used according to the invention are prepared by, for example, extending the active compound with solvents, vehicles and/or propellant gases, where appropriate using emulsifiers and/or dispersing agents.

Examples of auxiliaries which may be mentioned are: water, non-toxic organic solvents, such as paraffins (for example petroleum fractions), vegetable oils (for example groundnut/sesame oil), alcohols (for example ethyl alcohol and glycerol), glycols (for example propylene glycol and polyethylene glycol), solid vehicles, such as, for example, natural rock powders (for example highly disperse silica and silicates), sugars (for example crude sugar, lactose and glucose); emulsifiers, such as non-ionic and anionic emulsifiers (for example polyoxyethylene fatty acid esters and polysulphonates), dispersing agents (for example lignin, sulphite waste liquors, methylcellulose, starch and polyvinylpyrrolidone) and lubricants (for example magnesium stearate, talc, stearic acid and sodium lauryl sulphate, propellant gases (for example Frigens, nitrogen, nitrous oxide, propane, butane or $CO_2$).

Administration is effected in the customary manner, preferably enterally or parenterally, in particular by inhalation.

In the case of enteral administration, tablets can, of course, also contain, in addition to the vehicles mentioned, additives such as sodium citrate, calcium carbonate and dicalcium phosphate, together with various additional substances, such as starch, preferably potato starch, gelatin and the like. Furthermore, lubricants such as magnesium stearate, sodium lauryl sulphate and talc can also be used when making tablets. In the case of aqueous suspensions and/or elixirs which are intended for oral use, the active compounds can be mixed with various flavor-improving agents or colorants.

In the case of parenteral administration, solutions of the active compound, employing suitable liquid vehicles, can be used. For inhalation, it is possible to use the active compounds both as the pure substance and as a solution, using suitable propellant gases.

Surprisingly, even at low doses, the substances used according to the invention show in biological tests relaxation of the contracted bronchial musculature without the occurrence of the cardiovascular effects as is the case with other dihydropyridines.

By way of example, the action of the substances used according to the invention is shown by the following test results with methyl 1,4-dihydro-2,6-dimethyl-5-methylsulphonyl-4-(2-nitrophenyl)pyridine-3-carboxylate (called A below):

(1) Studies on isolated tracheal rings from normal guinea pigs:

The carbachol-induced contraction of the tracheal rings of guinea pigs is inhibited by substance A as a function of the concentration. The $IC_{50}$ value is $1.1 \times 10^{-7}$ g/ml.

(2) Studies on isolated human bronchial muscle:

Isolated human bronchial muscles are contracted with $10^{-7}$ g/ml carbachol. Addition of substance A reduces, as a function of the concentration, the contraction. The $IC_{50}$ value is $6 \times 10^{-8}$ g/ml.

It is understood that the specification and examples are illustrative but not limitative of the present invention and that other embodiments within the spirit and scope of the invention will suggest themselves to those skilled in the art.

We claim:
1. A method of treating a patient suffering from asthma which comprises administering to such patient an asthma-relieving amount of a 5-sulphonyl-1,4-dihydropyridine of the formula

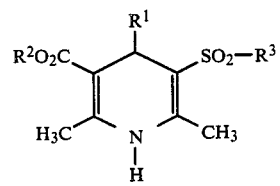

in which
- $R^1$ is aryl having 6 or 10 C atoms, optionally substituted by 1 to 3 identical or different substituents selected from the group consisting of halogen, cyano, nitro, trifluoromethyl, trifluoromethoxy, alkoxycarbonyl having up to 4 C atoms, carboxyl, alkoxy having up to 4 C atoms or straight-chain or branched alkyl having up to 4 C atoms, or is pyridyl, thienyl, furyl or benzoxadiazolyl,
- $R^2$ is straight-chain, branched or cyclic, saturated or unsaturated alkyl having up to 7 C atoms, which can be interrupted in the chain by 1 or 2 oxygen and/or sulphur atoms, and which is optionally substituted by halogen, nitro, cyano, carboxyl, alkoxycarbonyl with up to 4 C atoms, aryl having, 6 or 10 C atoms, or an amino group, it being possible for the amino group to carry 1 or 2 identical or different substituents from the group comprising alkyl with up to 4 C atoms, aryl having 6 to 10 C atoms or alkaryl having 7 to 10 C atoms,
- $R^3$ is aryl having 6 to 10 C atoms which can optionally be substituted by 1 to 3 identical or different substitutents selected from the group consisting of halogen, cyano, nitro, trifluoromethyl, trifluoromethoxy, alkoxy having up to 4 C atoms, or dialkylamino, or is a straight-chain, branched or cyclic alkyl having up to 8 C atoms, which can optionally be substituted by cyano, halogen or nitro.

2. A method according to claim 1, in which
- $R^1$ is phenyl which can optionally be substituted by 1 to 2 identical or different substituents selected from the group consisting of fluorine, chlorine, bromine, nitro, cyano, trifluoromethyl, trifluoromethoxy, alkoxy having up to 2 C atoms or alkyl having up to 2 C atoms, or is pyridyl, thienyl, furyl or benzoxadiazolyl,
- $R^2$ is straight-chain, branched or cyclic, saturated or unsaturated alkyl having up to 6 C atoms, which can optionally be interrupted in the chain by 1 to 2 oxygen and/or sulphur atoms, and which can optionally be substituted by 1 to 3 identical or different substituents selected from the group consisting of fluorine, chlorine, bromine, cyano, nitro, alkoxycarbonyl having up to 2 C atoms, phenyl or an amino group, it being possible for the amino group to be substituted by one or two identical or different substituents selected from the group consisting of alkyl having up to 2 C atoms or benzyl, and
- $R^3$ is phenyl which can optionally be substituted by 1 to 2 identical or different substituents selected from the group consisting of fluorine, chlorine, bromine, nitro, trifluoromethyl, cyano, trifluoromethoxy or alkyl having up to 2 C atoms, or is a straight-chain, branched or cyclic alkyl having up to 7 C atoms which can optionally be substituted by fluorine, chlorine, bromine, cyano or nitro.

3. A method according to claim 1, in which
- $R^1$ is phenyl which is optionally substituted by 1 to 2 chlorine, cyano, nitro or trifluoromethyl or is pyridyl,
- $R^2$ is straight-chain or branched alkyl having up to 5 C atoms, which can optionally be interrupted by an oxygen and/or sulphur atom, and which can optionally be substituted by one, two or three substitutent selected from the group consisting of fluorine, cyano or the benzylmethylamino group, and
- $R^3$ is phenyl which is optionally substituted by 1 to 2 chlorine, nitro, cyano or trifluoroemthyl, or is methyl or ethyl, it being possible for ethyl optionally to be substituted by one to three fluorine.

4. A method according to claim 1, wherein such dihydropyridine is ethyl 1,4-dihydro-2,6-dimethyl-5-phenyl-sulphonyl-4-(2-trifluoromethylphenyl) pyridine-3-carboxylate, 5. A method according to claim 1, wherein such dihydropyridine is (2-ethylthio)ethyl 1,4-dihydro-2,6-dimethyl-5-methylsulphonyl-4-(3-nitrophenyl)pyridine-3-carboxylate, 6. A method according to claim 1, wherein such dihydropyridine is methyl 1,4-dihydro-2,6-dimethyl-5-methyl-sulphonyl-4-(2-nitrophenyl) pyridine-3-carboxylate.

* * * * *